United States Patent [19]

Torii et al.

[11] Patent Number: 4,958,018
[45] Date of Patent: Sep. 18, 1990

[54] METHOD FOR PRODUCTION OF 3-EXOMETHYLENECEPHAM DERIVATIVES

[75] Inventors: Sigeru Torii; Hideo Tanaka, both of Okayama; Masatoshi Taniguchi, Suita; Michio Sasaoka, Tokushima; Norio Saito, Tokushima; Takashi Shiroi, Tokushima; Shigemitsu Nagao, Mobara; Ryo Kikuchi, Tokushima; Yutaka Kameyama, Tokushima, all of Japan

[73] Assignee: Otsuka Kagaku Kabushiki Kaisha, Osaka, Japan

[21] Appl. No.: 347,319

[22] Filed: May 4, 1989

[30] Foreign Application Priority Data

May 11, 1988 [JP] Japan .................................. 63-115711

[51] Int. Cl.$^5$ .......................................... C07D 501/04
[52] U.S. Cl. .................... 540/215; 540/221; 540/222
[58] Field of Search .................. 540/215, 222, 221

[56] References Cited

FOREIGN PATENT DOCUMENTS

| | | |
|---|---|---|
| 57-70893 | 5/1982 | Japan . |
| 58-222092 | 12/1983 | Japan . |
| 59-46952 | 11/1984 | Japan . |
| 60-187689 | 9/1985 | Japan . |
| 61-53289 | 3/1986 | Japan . |

*Primary Examiner*—Nicholas S. Rizzo
*Attorney, Agent, or Firm*—Armstrong, Nikaido Marmelstein, Kubovcik & Murray

[57] ABSTRACT

Disclosed is a method of producing a 3-exomethylenecepham of the formula

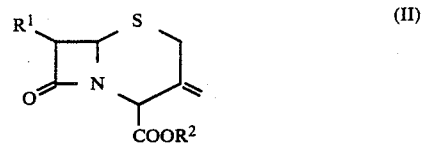

wherein $R^1$ is amino or substituted amino and $R^2$ is a carboxy-protecting group comprising reacting a cephem of the formula

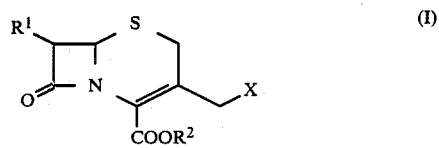

wherein $R^1$ and $R^2$ are as defined above and X is halogen with lead metal while maintaining the pH of the reaction system at about 0.1 to 8. The cephem (I) may be reacted with a catalytic amount of lead metal or a lead compound in the presence of a metal having a greater ionization tendency than lead.

17 Claims, No Drawings

METHOD FOR PRODUCTION OF 3-EXOMETHYLENECEPHAM DERIVATIVES

This invention relates to a method for production of 3-exomethylenecepham derivatives which are of value as intermediates for the production of 3-cephem antibiotics. More particularly, this invention relates to a method of producing the 3-exomethylenecepham derivative of the general formula

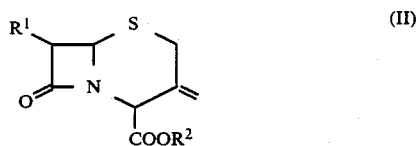 (II)

wherein $R^1$ is an amino group or a substituted amino group and $R^2$ is a carboxy-protecting group, from a cephem derivative of the general formula

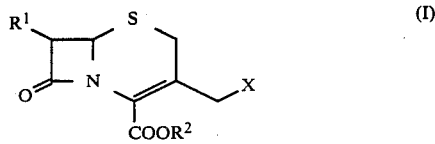 (I)

wherein $R^1$ and $R^2$ have the meanings respectively defined above and X is a halogen atom.

The hitherto-known methods for production of a 3-exomethylenecepham derivative of general formula (II) from a cephem derivative of general formula (I) include the electrolytic reduction method (Unexamined Japanese Patent Publication (KOKAI) No. 187689/1985) and the chemical reduction method employing a metal and an acid in combination (for example, Examined Japanese Patent Publication No. 46952/1984, Unexamined Japanese Patent Publications (KOKAI) No. 70893/1982, KOKAI No. 222092/1983 and KOKAI No. 53289/ 1986).

However, the electrolytic reduction method, the former, is disadvantageous in that it is not universably applicable because special equipment is required and the maintenance and control of the equipment are difficult, thus rendering it difficult to practice on a commercial scale.

The chemical reduction method also has the following disadvantages. Thus, the known metals for use in this method include Fe, Zn, Sn (Examined Japanese Patent Publication No. 46952/1984 and Unexamined Japanese Patent Publication (KOKAI) No. 222092/1983), Ti+++ (Unexamined Japanese Patent Publication (KOKAI) No. 70893/1982) and Mg (Unexamined Japanese Patent Publication (KOKAI) No. 53289/1986). While these metals must be used in stoichiometric amounts, the use of such metals, particularly heavy metals, in large amounts presents pollution problems and for this reason it is difficult to practice the method on a commercial scale. In the case of Fe and Mg which are considered to present no pollution problem, there is a total disadvantage that the yield of the product compound is low. Particularly in the case of Fe, the corresponding patent literature, Examined Japanese Patent Publication No. 46952/1984, contains no relevant working example. Moreover, attempts to reduce a compound of general formula (I) using Fe were only rewarded with a very sparse progress of the reduction reaction, with the starting compound (I) being recovered intact (refer to Comparative Examples 1 and 2 which appear hereinafter). Thus, Fe is not a metal that can be used advantageously for the purposes of this invention.

With Mg, too, the yield of the desired compound is about 71.6% at best and the purity of the compound is also not sufficiently high, namely about 93.7% (refer to Example 1 of Unexamined Japanese Patent Publication (KOKAI) No. 53289/1986). Furthermore the carboxyl group of the starting compound (I) used in Example 1 of Unexamined Japanese Patent Publication (KOKAI) No. 53289/1986 is not protected. Our verification experiments showed that when the compound (I) with this carboxyl group protected is subjected to reduction under the same conditions as Example 1 of the above patent publication, the reduction reaction does not proceed to an appreciable extent, with the intact starting compound (I) being recovered (see Comparative Examples 3 and 4 which appear hereinafter).

It is an object of this invention to provide an expedient and commercially advantageous method for producing the 3-exomethylenecepham derivative of general formula (II) in high yield and high purity.

This invention is accordingly directed to a method of producing a 3-exomethylenecepham derivative of the general formula:

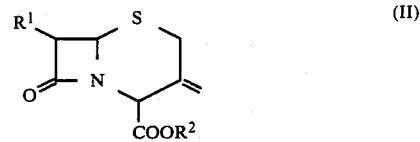 (II)

wherein $R^1$ is an amino group or a substituted amino group and $R^2$ is a carboxy-protecting group, which comprises reacting a cephem derivative of the general formula

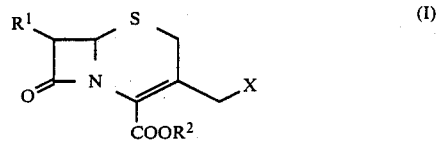 (I)

wherein $R^1$ and $R^2$ have the meanings respectively defined above and X is a halogen atom with lead metal in an inert organic solvent capable of dissolving said cephem derivative or a mixture of such solvent with water at pH 0.1 to 8.

This invention is further directed to a method for producing a 3-exomethylenecepham derivative of general formula (II) which comprises reacting a cephem derivative of general formula (I) with a catalytic amount of lead metal or a lead compound in the presence of a metal having a greater ionization tendency than lead in an inert organic solvent capable of dissolving said cephem derivative or a mixture of such inert organic solvent with water at pH of between 0.1 and 8.

The intensive research of the inventors of this invention revealed that lead metal, which has heretofore been scarcely used as a reducing agent, is an excellent reducing agent for the purposes of this invention. It was also found that when a metal having a greater ionization tendency than lead is present in the reaction system, not only lead metal but various compounds of lead can be used as reducing agents and, moreover, the necessary amount of the lead metal or lead compound can be drastically decreased to virtually overcome the pollution problem associated with lead metal. This invention has been accomplished based on the above findings.

In accordance with this invention, a 3-exomethylenecepham derivative of general formula (II) can be expediently produced, in high yield and purity and without entailing a byproduct, by reacting a cephem derivative of general formula (I) with lead metal in an organic solvent or a mixture of an organic solvent with water, with pH adjustment by addition of an acid if necessary, or alternatively by reacting (I) with a catalytic amount of lead metal or a compound of lead in the presence of a metal having a greater ionization tendency than lead.

In this specification, X means a halogen atom such as Cl, Br and I.

$R^1$ means an amino group or a substituted amino group. Examples of said substituted amino group include benzamido which may be nuclearly substituted by halogen, nitro, hydroxy or lower alkoxy (particularly $C_{1-4}$ alkoxy), such as benzamido, o-chlorobenzamido, m-chlorobenzamido, p-chlorobenzamido, o-nitrobenzamido, p-nitrobenzamido, o-hydroxybenzamido, m-hydroxybenzamido, p-hydroxybenzamido, o-methoxybenzamido, m-methoxybenzamido, p-methoxybenzamido, etc., phenylglycylamido, amino-protected phenylglycylamido, p-hydroxyphenylglcylamido, amino-protected p-hydroxyphenylglycylamido, α-sulfonylphenylacetamido, α-hydroxyphenylacetamido, α-carbamoylphenylacetamido, phenylacetamido which may be nuclearly substituted by lower alkoxy (particularly $C_{1-4}$ alkoxy), halogen or hydroxy, such as phenylacetamido, o-methoxyphenylacetamido, m-methoxyphenylacetamido, p-methoxyphenylacetamido, o-chlorophenylacetamido, m-chlorophenylacetamido, p-chlorophenylacetamido, p-hydroxyphenylacetamido, o-hydroxyphenylacetamido, m-hydroxyphenylacetamido, etc., α-naphthylacetamido, β-naphthylacetamido, phenoxyacetamido which may be nuclearly substituted by halogen or lower alkoxy (particularly $C_{1-4}$ alkoxy), such as phenoxyacetamido, o-chlorophenoxyacetamido, m-chlorophenoxyacetamido, p-chlorophenoxyacetamido, o-bromophenoxyacetamido, m-bromophenoxyacetamido, p-bromophenoxyacetamido, o-methoxyphenoxyacetamido, m-methoxyphenoxyacetamido, p-methoxyphenoxyacetamido, etc., tetrazolylacetamido, thienylacetamido, 2-aminothiazolylacetamido, amino-protected 2-aminothiazolylacetamido, furylacetamido, and protected amino.

Referring to the above-mentioned amino-protected phenylglycylamido, amino-protected p-hydroxyphenylglycylamido, amino-protected 2-aminothiazolylacetamido and protected amino, the protective group in each protected amino may be selected from among those protective groups described by Theodora W. Green: "Protective Groups in Organic Synthesis", Chapter 7. As typical examples of the protected amino group, there may be mentioned methylcarbamato, 9-fluorenylmethylcarbamato, 2,2,2-trichloroethylcarbamato, 2-trimethylsilylethylcarbamato, 1,1-dimethylpropylcarbamato, 1,1-dimethyl-2-cyanoethylcarbamato, tert-butylcarbamato, 1-adamantylcarbamato, benzylcarbamato, p-nitrobenzylcarbamato, diphenylmethylcarbamato, phthalimido, 2,3-diphenylmaleimido, N-phenacylamino, N-methoxymethylamino, N-2-chloroethoxymethylamino, N-benzyloxymethylamino, N-pivaloyloxymethylamino, N-benzylamino, N-o-nitrobenzylamino, N-di(p-methoxyphenyl)methylamino, N-triphenylmethylamino, N-(diphenyl-4-pyridylmethyl)amino, N-trimethylsilylamino, N-tert-butyldimethylsilylamino, benzenesulfenamido, p-methoxybenzenesulfonamido and phenacylsulfonamido.

Examples of the carboxy-protecting group represented by $R^2$ are lower alkyl, particularly $C_{1-4}$ alkyl, such as methyl, ethyl, propyl, isopropyl, butyl, tert-butyl, etc., substituted methyl such as methylthiomethyl, phenacyl, p-bromophenacyl, α-methylphenylacyl, p-methoxyphenacyl, —CH(COCH$_3$)$_2$, —CH(COCH$_3$)COOCH$_3$, —CH(COCH$_3$)COOC$_2$H$_5$, —CH(COCH$_3$)CO-phenyl, N-phthalimidomethyl, etc., substituted ethyl such as 2,2,2-trichloroethyl, 2-chloroethyl, 2-bromoethyl, 2-(trimethylsilyl)ethyl, 2-methylthioethyl, 2-(p-nitrophenylsulfenyl)ethyl, 2-(p-toluenesulfonyl)ethyl, cumyl, etc., cycloalkyl, particularly $C_{3-8}$ cycloalkyl, such as cyclopentyl, cyclohexyl, etc., allyl, substituted allyl such as cinnamyl etc., phenyl, substituted phenyl such as p-methylthiophenyl etc., benzyl, substituted benzyl such as triphenylmethyl, diphenylmethyl, bis(o-nitrophenyl)methyl, 9-anthrylmethyl, 2-(9,10-dioxo)anthrylmethyl, 5-dibenzosuberyl, 2,4,6-trimethylbenzyl, p-bromobenzyl, o-nitrobenzyl, p-nitrobenzyl, p-methoxybenzyl, piperonyl, etc., 4-picolyl, and substituted silyl such as trimethylsilyl, tert-butyldimethylsilyl, triethylsilyl, isopropyldimethylsilyl, phenyldimethylsilyl, etc.

In accordance with the invention, the above-mentioned cephem derivative of general formula (I) is reacted with lead metal.

The starting compound of general formula (I) is either a compound known in the art or a compound which can be synthesized by an appropriate known process.

The form or shape of lead metal, which is to be reacted with the compound of general formula (I), is not particularly critical. Thus, lead metal may be used in a variety of forms, for example in powder, sheet, lump or wire-like form. However, for driving the reaction to completion at a lower temperature and in a shorter period of time, the use of powder-form lead metal is advantageous. The powdery lead metal may have a particle size selected within a wide range, but preferably have a particle size of between about 10 and 500 mesh (according to JIS G3555-1964). The lead metal is used generally in an amount of about 1 to 10 moles, preferably about 1 to 4 moles, per mole of the compound of general formula (I).

In a preferred embodiment of the invention, the reaction can be carried out in the presence of a metal having a greater ionization tendency than lead. The use of such metal in the reaction system can reduce the necessary amount of lead metal to an extremely low level, whereby the workup following the reaction step becomes easier and in addition, the reduction reaction can be conducted at a lower temperature and within a shorter period of time. Preferred examples of the metal having a greater ionization tendency than lead are iron, nickel, tin, cobalt, magnesium and aluminum, among others. In the practice of the invention, these metals may be used either singly or in combination (as a mixture of two or more of them). Among these, aluminum is most preferred from the reaction efficiency, ease of handling during reaction and workup, pollution control and other viewpoints. The form or shape of these metals is also not particularly critical. Thus, they may be used in a variety of forms, for example in powder, sheet, foil, lump or wire-like form. For smooth progress of the reaction, however, the powder form is advantageous. The metals in powder form may have a particle size selected within a wide range, but preferably have a particle size of between about 10 and 300 mesh (according to JIS G3555-1964). These metals are used generally in an amount of about 1 to 50 moles, preferably about 1 to 5 moles, per mole of the compound of general formula (I).

When a metal having a greater ionization tendency than lead is used combinedly in accordance with the invention, various lead compounds may be used in lieu of lead metal. The lead atom in said lead compounds may have a valence of 0, 2 or 4. These lead compounds may be used in the form of a hydrate. A wide range of hitherto known lead compounds can be used as said lead compounds. As examples, there may be mentioned lead halides such as lead fluoride, lead chloride, lead bromide and lead iodide, lead salts of inorganic acids, such as lead nitrate, lead sulfate, lead perchlorate, lead borate, lead carbonate and lead phosphate, lead salts of aliphatic carboxylic acids, particularly of $C_{1-20}$ aliphatic carboxylic acids, such as lead acetate, lead oxalate, lead stearate, etc., lead oxide, lead hydroxide, and lead complexes in which the lead atom has a valence of 0, 2 or 4. The ligands in said complexes include, among others, chelating agents such as ethylenediaminetetraacetic acid, nitrilotriacetic acid, dithizone, acetylacetone, acetoacetic acid, methyl acetoacetate, ethyl acetoacetate, triethanolamine, dimethylglyoxime, oxine, etc., compounds capable of serving as ligands via an oxygen, nitrogen or phosphorus atom, such as ketones, esters, carboxylic acids, amines, oximes, ammonia, nitriles, organic phosphines (such as triphenylphosphine), etc. These lead compounds may be used either singly or in combination.

Where a metal having a greater ionization tendency than lead is used in combination, the presence of a very small amount of lead metal or a lead compound in the reaction system is sufficient as a matter of fact while a theory would require the presence of one lead atom or one lead compound molecule. Generally, the lead metal or lead compound is used recommendably in an amount of about 0.00001 to 0.5 mole, preferably about 0.0001 to 0.2 mole, per mole of the compound of general formula (I).

Either in the case of using lead metal alone or in the case of using lead metal or a lead compound in combination with a metal having a greater ionization tendency than lead, the reduction reaction according to the invention is carried out in an organic solvent or a water-containing organic solvent or, if the organic solvent used is not completely miscible with water, in a two-layer (organic solvent-water) system, with an acid added to the reaction system if so desired. The organic solvent may be selected from among a variety of known organic solvents capable of dissolving the compound of general formula (I) and capable of remaining inert under the conditions of said reaction. Examples are alcohols, particularly $C_{1-4}$ saturated aliphatic alcohols, such as methanol, ethanol, propanol, isopropanol, butanol, tert-butanol, etc., lower alkyl esters of lower carboxylic acids, particularly $C_{1-4}$ alkyl esters of $C_{1-4}$ carboxylic acids, such as methyl formate, ethyl formate, propyl formate, butyl formate, methyl acetate, ethyl acetate, propyl acetate, butyl acetate, methyl propionate, ethyl propionate, etc., ketones, particularly di($C_{1-4}$ alkyl) ketones, such as acetone, methyl ethyl ketone, methyl propyl ketone, methyl butyl ketone, methyl isobutyl ketone, diethyl ketone, etc., ethers, for example di($C_{1-4}$ alkyl) ethers such as diethyl ether, ethyl propyl ether, ethyl butyl ether, dipropyl ether, diisopropyl ether, dibutyl ether, etc., ethylene glycol mono or di($C_{1-4}$ alkyl) ethers such as methylcellosolve, dimethoxyethane, etc., and cyclic ethers such as tetrahydrofuran, dioxane, etc., nitriles, particularly $C_{2-5}$ alkylnitriles, such as acetonitrile, propionitrile, butyronitrile, isobutyronitrile, valeronitrile, etc., substituted or unsubstituted aromatic hydrocarbons, particularly benzene which may have one to three substituents selected from the group consisting of methyl, halogen and methoxy, such as benzene, toluene, xylene, chlorobenzene, anisole, etc., halogenated hydrocarbons, particularly halogenated $C_{1-4}$ hydrocarbons, such as dichloromethane, chloroform, dichloroethane, trichloroethane, dibromoethane, propylene dichloride, carbon tetrachloride, freons, etc., aliphatic hydrocarbons, particularly $C_{5-10}$ aliphatic hydrocarbons, such as pentane, hexane, heptane, octane, etc., cycloalkanes, particularly $C_{5-10}$ cycloalkanes, such as cyclopentane, cyclohexane, cycloheptane, cyclooctane, etc., amides such as dimethylformamide, dimethylacetamide, etc., and dimethyl sulfoxide. These may be used either singly or in admixture. These organic solvents may contain water if necessary. Recommendably, such solvents are used in an amount of about 0.5 to 200 liters, preferably about 1 to 50 liters, per kilogram of the compound of general formula (I).

Either in the case of using lead metal alone or in the case of using lead metal or a lead compound in combination with a metal having a greater ionization tendency than lead, the reduction reaction according to the invention is carried out while maintaining the pH of the reaction system at about 0.1 to 8, preferably about 2 to 7, throughout the reaction. In the specification and claims, the term "pH of the reaction system" refers to the pH value obtained by diluting a portion of the reaction mixture 10-fold with water and measuring the pH value of the diluted reaction mixture. The pH of the reaction system can be adjusted to a desired value with an organic or inorganic acid or preferably with a salt of such organic or inorganic acid capable of giving an acidic aqueous solution. As said organic acid, there may be mentioned, among others, carboxylic acids such as formic acid, acetic acid, propionic acid, oxalic acid, tartaric acid, malic acid, benzoic acid, malonic acid, monochloroacetic acid, dichloroacetic acid, trichloroacetic acid, trifluoroacetic acid, trimellitic acid, etc., sulfonic acids such as benzenesulfonic acid, toluenesulfonic acid, naphthalenesulfonic acid, methanesulfonic acid, trifluoromethanesulfonic acid, chloromethanesulfonic acid, o-benzenedisulfonic acid, etc., sulfinic acids such as benzenesulfinic acid, toluenesulfinic acid, 1,2-cyclohexanediamine-N,N,N',N'-tetraacetic acid, dihydroxyethylglycine, diaminopropanoltetraacetic acid, hydroxyethylethylenediaminetriacetic acid, ethylenediaminetetraacetic acid, hydroxyethyliminodiacetic acid, amino acids such as L-glutamic acid, glycylglycine, L-tyrosine, etc., and acidic compounds such as ascorbic acid, Meldrum's acid, squaric acid, pyromeconic acid, malonic acid lower (e.g. $C_{1-4}$) alkyl esters, acetylacetic acid lower (e.g. $C_{1-4}$) alkyl esters, phenol, cresol, barbituric acid, etc. The inorganic acid includes, among others, hydrochloric acid, sulfuric acid, nitric acid, perchloric acid, hydrobromic acid, hydroiodic acid, hydrofluoric acid, bromous acid, bromic acid, hypochlorous acid, hypobromous acid, phosphoric acid, phosphorous acid, methaphosphoric acid, silicic acid and boric acid. As said salt of such organic or inorganic acid capable of giving an acidic aqueous solution, there may be mentioned, for example, the ammonium salt and mono-, di-, tri- or tetra(lower(e.g. $C_{1-4}$)alkyl)ammonium salt. Such acids or salts thereof capable of giving an acidic aqueous solution may be used either alone or in combination. For attaining a desired pH, it is generally advantageous to use such acid salt capable of giving an acidic aqueous solution in an amount of about 1 to 10 moles, preferably about 1 to 3 moles, per mole of the starting compound of general formula (I). By using about 0.0001 to 0.5 mole, preferably about 0.001 to 0.2 mole, per mole of the compound of general formula (I), of an organic or inorganic acid such as mentioned above in combination with said salt, it is possible to drive the reaction according to the invention to completion at a lower temperature and in a shorter period of time. Where a metal having a greater ionization tendency than lead is used combinedly, said reaction can be completed with a still smaller amount of lead metal or a lead compound if a small amount of an acid is used together with said salt.

The reaction temperature range optimal for the reaction according to the invention may vary depending on the starting material, solvent and other factors. Generally, however, the range of about $-20°$ C. to $80°$ C., preferably about $0°$ C. to $50°$ C., is suitable.

When carried out under application of ultrasonic waves, the reaction according to the invention may proceed more rapidly in some instances.

After completion of the above reaction, the desired 3-exomethylenecepham derivative of general formula (II) can be isolated in an almost pure form, for example by an ordinary extraction procedure. Further purification, if necessary, can be effected by a conventional purification means, such as recrystallization, column chromatography, etc. The 3-exomethylenecepham derivative of general formula thus obtained (II) thus obtained can be converted, for example to an antiobiotic of the formula

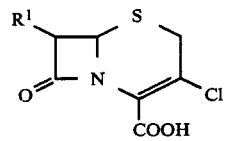

for example by ozonolysis to give a 3-hydroxycephem derivative, which is then converted by a chlorinating agent such as thionyl chloride to a 3-chlorocephem derivative, followed by de-protection of 4-position carboxyl group. See J.A.C.S., 96, 4986, 1974.

The advantageous features of the method according to the invention may be summarized as follows:

(1) The desired 3-exomethylenecepham derivative of general formula (II) can be produced in very high selectivity and yield, so that no particular purification is required in most cases.

(2) The desired 3-exomethylenecepham derivative of general formula (II) can be produced in readily available equipment by a simple and easy procedure without the need of any special apparatus.

(3) While, when to be carried out on a commercial scale, a process involving the use of a heavy metal is subject to various restrictions from the pollution control viewpoint, the method according to the invention makes it possible to reduce the amount of lead metal or lead compound to a minimum through the conjoint use of a metal which presents no pollution problem. The workup following the reaction is also simplified and facilitated accordingly.

As mentioned above, the method according to the invention is commercially very advantageous in producing the 3-exomethylenecepham derivative of general formula (II).

The following examples are further illustrative of the present invention. In the examples, mesh size is one according to JIS G3555-1964.

EXAMPLE 1

To a solution of 0.5 g of a compound of general formula (I) in which $R^1$ is phenylacetamido, $R^2$ is p-methoxybenzyl and X is chlorine [hereinafter referred to as "compound (Ia)"] in a mixture of 4 ml of tetrahydrofuran and 1 ml of water, there were added 0.16 g of ammonium chloride, 0.01 g of lead powder which can pass a 200 mesh sieve and 0.08 g of aluminum powder which can pass a 20 mesh sieve, and the reaction was carried out at $40°$ C. for 1.5 hours. The pH of the reaction system was in the range of 5–7 throughout the reaction. The insoluble matter was filtered off, the filtrate was extracted with ethyl acetate, and the extract was washed with diluted hydrochloric acid, then dried over anhydrous sodium sulfate and concentrated under reduced pressure to give a compound of general formula (II) in which $R^1$ is phenylacetamido and $R^2$ is p-methoxybenzyl [hereinafter referred to as "compound (IIa)"] as white crystals (yield 92%).

The NMR spectrum of this product was in good agreement with that of compound (IIa) synthesized by a known method. The purity of said product as estimated by HPLC (high performance liquid chromatography) was 98.5%.

COMPARATIVE EXAMPLE 1

To a solution of 0.5 g of compound (Ia) in 5 ml of dimethylformamide were added 0.2 ml of formic acid and 0.115 g of iron powder which can pass a 100 mesh sieve, and the reaction mixture was stirred at room temperature for 1.5 hours. However, the reaction failed to proceed and compound (Ia) was recovered unchanged.

COMPARATIVE EXAMPLE 2

To a solution of 0.5 g of compound (Ia) in a mixture of 4 ml of dimethylformamide and 0.5 ml of water were added 0.16 g of ammonium chloride and 0.069 g of iron powder which can pass a 100 mesh sieve, and the reaction was carried out at $40°$ C. for 1.5 hours under application of ultrasonic waves (0.29 w/cm$^2$, 42 kHz). The pH of the reaction system was in the range of 5 to 6 throughout the reaction.

The reaction mixture obtained was analyzed by HPLC and it was found that the yield of compound (IIa) and that of the corresponding 3-methyl-3-cephem compound, an isomer of compound (IIa) as resulting from double bond migration, were only 5% and 2%, respectively, based on the starting compound (Ia), and the rest was unreacted compound (Ia).

COMPARATIVE EXAMPLE 3

Compound (Ia) was treated as described in Example 1 of Unexamined Japanese Patent Publication (KOKAI) No. 53289/1986. The reaction did not proceed but compound (Ia) was recovered in its intact form.

COMPARATIVE EXAMPLE 4

To a solution of 0.5 g of compound (Ia) in a mixture of 4 ml of tetrahydrofuran and 1 ml of water were added 0.407 g of ammonium sulfate, 0.5 ml of 75% phosphoric acid and 0.1 g of magnesium powder which can pass a 20 mesh sieve, and the reaction mixture was stirred at 25° C. for 3 hours. The pH of the reaction system was in the range of 0.1 to 1 throughout the stirring operation. However, the reaction failed to proceed and compound (Ia) was recovered intact.

EXAMPLE 2

To a solution of 5 g of compound (Ia) in a mixture of 20 ml of tetrahydrofuran and 5 ml of water were added 0.65 g of ammonium chloride, 0.014 g of dl-malic acid, 0.01 g of lead chloride and 0.332 g of aluminum powder which can pass a 20 mesh sieve, and the reaction was carried out at 40° C. for 4 hours under application of ultrasonic waves (0.29 w/cm$^2$, 42 kHz). The pH of the reaction system was in the range of 2 to 4 throughout the reaction. The reaction mixture was worked up in the same manner as in Example 1 to give compound (IIa) (yield 93%).

The NMR spectrum of this product was in agreement with that of compound (IIa) synthesized by a known method. The purity of the product as determined by HPLC was 98.5%.

EXAMPLE 3

A compound of general formula (I) in which $R^1$ is phenylacetamido, $R^2$ is p-methoxybenzyl and X is iodine was treated in the same manner as in Example 1 to give a compound of general formula (II) in which $R^1$ is phenylacetamido and $R^2$ is p-methoxybenzyl (yield 90%).

The purity of the product as determined by HPLC was 98.5%.

EXAMPLE 4

The compounds of general formula (I) that are shown below in Table 1 were each treated in the same manner as in Example 1. The corresponding compounds of general formula (II) were obtained in high yield and purity.

The yield and purity (by HPLC) of each product are shown in Table 1.

TABLE 1

| Run | $R^1$ | $R^2$ | X | Yield (%) | Purity (%) |
|---|---|---|---|---|---|
| 1 | Phenylacetamido | Diphenylmethyl | Cl | 92 | 99 |
| 2 | Phenylacetamido | Methyl | Cl | 93 | 99 |
| 3 | Phenylacetamido | tert-Butyl | Cl | 91 | 98.5 |
| 4 | Phenoxyacetamido | p-Methoxybenzyl | Cl | 92 | 98.5 |
| 5 | Phenoxyacetamido | Diphenylmethyl | Cl | 92 | 99 |
| 6 | Phenoxyacetamido | Methyl | Cl | 93 | 99 |
| 7 | 2-Thienylacetamido | p-Methoxybenzyl | Cl | 90 | 98.5 |
| 8 | Phthalimido | p-Methoxybenzyl | Cl | 93 | 98.5 |
| 9 | Amino | p-Methoxybenzyl | Cl | 87 | 95 |
| 10 | Benzamido | Diphenylmethyl | Cl | 92 | 99 |

EXAMPLE 5

To a solution of 0.5 g of compound (Ia) in 5 ml of N,N-dimethylformamide were added 0.1 ml of 90% formic acid and lead powder which can pass a 200 mesh sieve, and the reaction was conducted at 30° C. for 4 hours. The pH of the reaction system was in the range of 1 to 3 throughout the reaction. The reaction mixture was worked up in the same manner as in Example 1 to give compound (IIa) in a yield of 85%.

The NMR spectrum of this product was in agreement with that of compound (IIa) synthesized by a known method. The purity of the product as determined by HPLC was 98%.

We claim:

1. A method of producing a 3-exomethylenecepham derivative of the formula $$\begin{array}{c} R^1 \quad\quad S \\ \diagup\quad\diagdown\diagup\diagdown \\ \bigm|\quad\quad\bigm| \\ O \diagdown \diagup N \diagdown \diagup \diagdown \\ \quad\quad\bigm| \\ \quad\quad COOR^2 \end{array}$$ (II)

wherein
$R^1$ is an amino group or a substituted amino group selected from the group consisting of benzamido which may be nuclearly substituted by halogen, nitro, hydroxy or lower alkoxy, phenylglycylamido, amino-protected phenylglycylamido, p-hydroxyphenylglycylamido, amino-protected p-hydroxyphenylglycylamido, α-sulfonylphenylacetamido, α-hydroxyphenylacetamido, α-carbamoylphenylacetamido, phenylacetamido which may be nuclearly substituted by lower alkoxy, halogen or hydroxy, α-naphthylacetamido, δ-naphthylacetamido, phenoxyacetamido which may be nuclearly substituted by halogen or lower alkoxy, tetrazolylacetamido, thienylacetamido, 2-aminothiazolylacetamido, amino-protected 2-aminothiazolylacetamido, furylacetamido and protected amino wherein the protected amino group in each of said amino-protected phenylglycylamido, amino-protected p-hydroxyphenylglycylamido, amino-protected 2-aminothiazolylacetamido and protected amino is selected from the group consisting of methylcarbamato, 9-fluorenylmethylcarbamato, 2,2,2-trichloroethylcarbamato, 2-trimethylsilylethylcarbamato, 1,1-dimethylpropylcarbamato, 1,1-dimethyl-2-cyanoethylcarbamato, tertbutylcarbamato, 1-adamantylcarbamato, benzylcarbamato, p-nitrobenzylcarbamato, diphenylmethylcarbamato, phthalimido, 2,3-diphenylmaleimido, N,phenacylamino, N-methoxymethylamino, N-2-chloroethoxymethylamino, N-benzyloxymethylamino, N-pivaloyloxymethylamino, N-benzylamino, N-o-nitrobenzylamino, N-di(p-methoxyphenyl)methylamino, N-triphenylmethylamino, N-(diphenyl-4-pyridylmethyl)amino, N-trimethylsilylamino, N-tert-butyldimethylsilylamino, benzenesulfenamido, p-methoxybenzene solfoamido and phenacylsulfonamido; and R² is a carboxy-protecting group, consisting essentially of reacting a cepham derivative of the formula

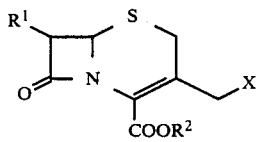

wherein
R¹ and R² are as defined above and X is a halogen atom, with lead metal at a temperature of about −20° C. to 80° C. in an inert organic solvent capable of dissolving said cephem derivative and capable of remaining inert under the condition of said reaction or in a mixture of such organic solvent and water while maintaining the pH of the reaction system at about 0.1 to 8.

2. A method as claimed in claim 1, wherein said lead metal is in the form of a powder having a particle size of between about 10 and 500 mesh according to JIS G3555-1964.

3. A method as claimed in claim 1, wherein said lead metal is used in an amount of about 1 to 10 moles per mole of the cephem derivative of formula (I).

4. A method as claimed in claim 1, wherein the cephem derivative of formula (I) is reacted with a catalytic amount of lead metal or a lead compound in the presence of a metal having a greater ionization tendency than lead.

5. A method as claimed in claim 4, wherein said metal having a greater ionization tendency than lead is at least one member selected from the class consisting of iron, nickel, tin, cobalt, magnesium and aluminum.

6. A method as claimed in claim 4, wherein the metal having a greater ionization tendency than lead is aluminum.

7. A method as claimed in claim 4, wherein the metal having a greater ionization tendency than lead is in the form of a powder having a particle size of between about 10 and 300 mesh according to JIS G3555-1964.

8. A method as claimed in claim 4, wherein said lead compound is at least one member selected from the class consisting of lead halides, lead salts of inorganic acids, lead salts of aliphatic carboxylic acids, lead oxide, lead hydroxide and lead complexes.

9. A method as claimed in claim 4, wherein the lead metal or lead compound is used in an amount of about 0.00001 to 0.5 mole per mole of the cephem derivative of formula (I).

10. A method as claimed in claim 4, wherein the reaction is carried out in a mixture of an organic solvent capable of dissolving the cephem derivative of formula (I) and water.

11. A method as claimed in claim 4, wherein the reaction is carried out while maintaining the pH of the reaction system at 2 to 7.

12. A method as claimed in claim 11, wherein the pH of the reaction system is adjusted with ah organic or inorganic acid or an organic or inorganic acid salt capable of giving an acidic aqueous solution.

13. A method as claimed in claim 4, wherein the reaction system contains an organic or inorganic acid salt capable of giving an acidic aqueous solution in an amount of about 1 to 10 moles per mole of the cephem derivative of formula (I) and an organic or inorganic acid in an amount of 0.0001 to 0.5 mole per mole of the cephem derivative of formula (I) and has a pH of about 2 to 7.

14. A method as claimed in claim 1, wherein the reaction is carried out at a temperature of about 0° C. to 50° C.

15. A method as claimed in claim 1, wherein the reaction is carried out under application of ultrasonic waves.

16. A method as claimed in claim 4, wherein the reaction is carried out at a temperature of about 0° C. to 50° C.

17. A method as claimed in claim 4, wherein the reaction is carried out under application of ultrasonic waves.

* * * * *